United States Patent [19]

Sayer

[11] 4,148,308

[45] Apr. 10, 1979

[54] MOUTHPIECE WITH A TONGUE RETRACTOR

[76] Inventor: William J. Sayer, 1618 Willow Rd., Palo Alto, Calif. 94304

[21] Appl. No.: 801,580

[22] Filed: May 31, 1977

[51] Int. Cl.² .............................................. A61B 13/00
[52] U.S. Cl. ..................................... 128/15; 128/147; 128/208
[58] Field of Search .................. 128/147, 145.5, 145.8, 128/136, 208, 201, 348 R, 351 R, 15, 16, 12, 13, 3, 4, 23, DIG. 29, 2.08

[56] References Cited

U.S. PATENT DOCUMENTS

| 3,154,069 | 10/1964 | Ring | 128/208 |
| 3,683,931 | 8/1972 | Chelucci et al. | 128/351 |
| 3,900,924 | 8/1975 | Meltzner | 128/16 |

FOREIGN PATENT DOCUMENTS

| 570994 | 2/1933 | Fed. Rep. of Germany | 128/147 |
| 669841 | 1/1939 | Fed. Rep. of Germany | 128/147 |

*Primary Examiner*—Henry J. Recla

[57] ABSTRACT

A mouthpiece comprising a tubular member about which a person may voluntarily place his lips in an air-tight manner for preventing a passage of air between the lips and the mouthpiece, said tubular member having a principal and a side air passageway and a blade-like member extending from one edge thereof, forming a tongue retractor for restricting the movement of the person's tongue and preventing it from obstructing a flow of air through the principal air passageway, is described. For evaluating respiratory processes, the cross-sectional area of the principal air passageway of the tubular member is large enough so as not to significantly affect the then current physiology of the respiratory process being evaluated. For use in administering medication, there is provided, in the interior wall of the mouthpiece, means, such as vanes or gun-barrel rifling, for controlling the air flow therethrough to the throat areas. To accommodate different sized mouths, the tongue retractor is adjustable in size and shape so as not to elicit significant gag reflex from the tongue or soft palate of the person using the mouthpiece and to fit comfortably between the interior edges of the person's teeth and gums along the right and left sides of the lower jaw.

14 Claims, 10 Drawing Figures

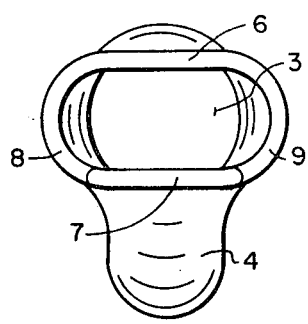
FIG. 5
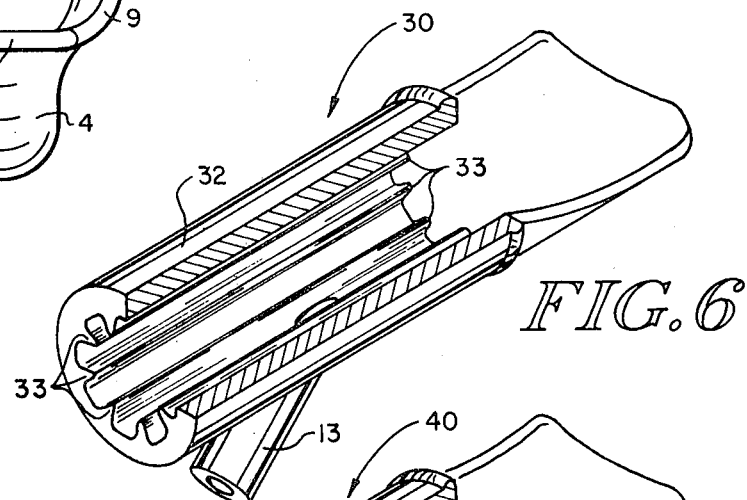
FIG. 6
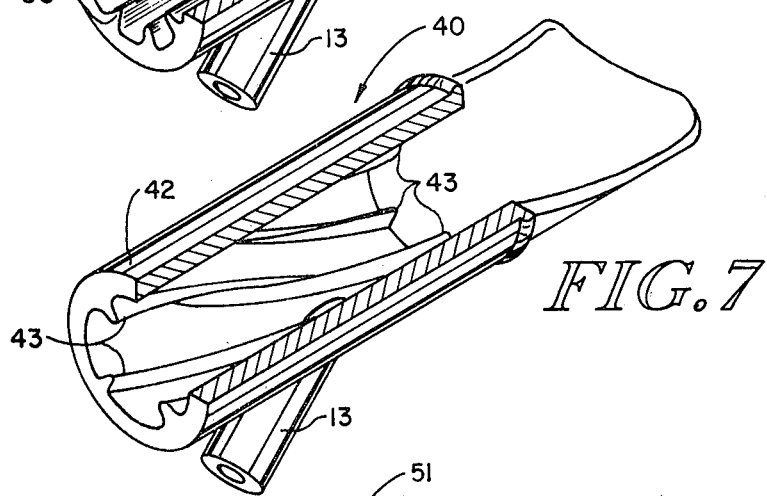
FIG. 7
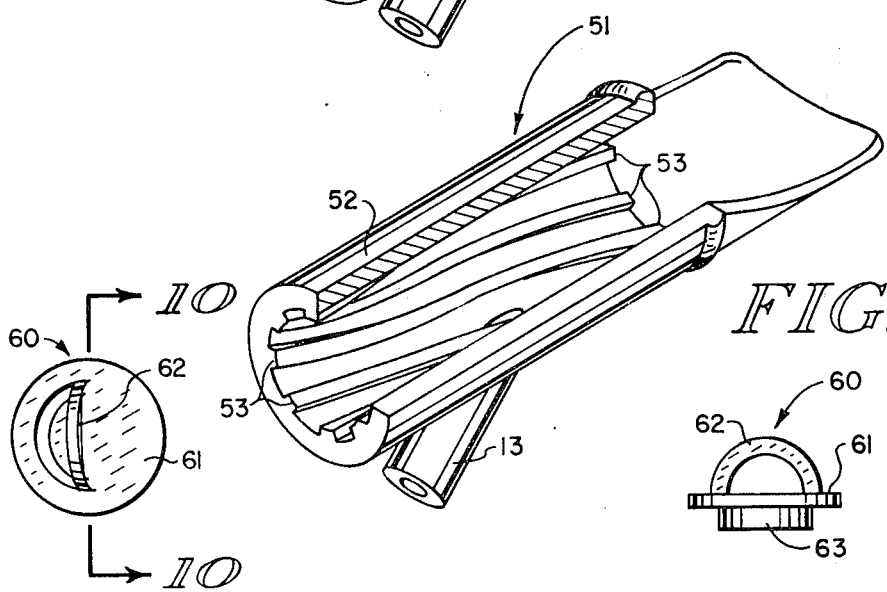
FIG. 8
FIG. 9
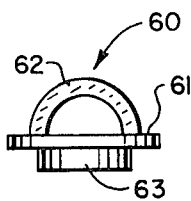
FIG. 10

MOUTHPIECE WITH A TONGUE RETRACTOR

BACKGROUND OF THE INVENTION

The present invention relates to mouthpieces in general and in particular to a mouthpiece, about which a person may place his lips in an air-tight manner, and a tongue retractor for use in diagnosing and treating conditions of the throat, tonsilar, respiratory tract and related areas, and for use in evaluating a person's respiratory processes.

Currently there are available a number of devices having means for retracting or which, in use, incidentally retract a person's tongue when used for diagnosing and treating physical conditions of the throat area. Among the most commonly known of the devices there is the common tongue blade. The common tongue blade comprises an elongated stick-like member, which is usually disposable, comprising wood or plastic material. It is most commonly used during physical examinations and is placed on the upper surface of the tongue to depress the tongue for viewing the throat and tonsilar areas. Ordinarily, a person being examined with a tongue blade is conscious and not anesthetized. Anesthetic is not required because the blade is generally not placed so far into the mouth of a person that a significant gag reflex is elicited. Another device used for diagnosing conditions of the throat area, in particular the larynx, is the laryngoscope. The laryngoscope, in use, is passed over the tongue, incidentally depressing or retracting the tongue for viewing of the vocal cords and larynx area. When the laryngoscope is used, the person being examined must either be unconscious or anesthetized because the placement of the laryngoscope does elicit a significant gag reflex.

Other devices which involve retracting a person's tongue include a grooved tongue depressor of a type commonly known as a mouth gag. Instruments of this type are used in connection with oral surgery and in particular in connection with oral surgery where anesthesia is administered by way of endotracheal tubation. A device of this type is described in a patent issued to W. H. Ring, U.S. Pat. No. 3,154,069, Oct. 27, 1964. Another device involving a means for retracting a person's tongue is an endotracheal tongue blade with tube guide. Such instruments are commonly used for simultaneously propping open the jaws and depressing the tongue while affording a fairly unobstructed access to a patient's oral and pharyngeal cavities. The tube guide portion of the device provides a guide through which an endotracheal tube may be passed into the trachea for anesthesia purposes, for applying suction to the trachea and bronchi, and for maintaining an open breathing passage through the pharynx and trachea, etc. A device of this type is disclosed in a patent issued to R. T. Barton, U.S. Pat. No. 2,756,742, July 31, 1956. In use, the patient in which the device is used must either be unconscious or anesthetized in order to prevent the elicitation of a significant gag reflex as described above with respect to the previously described tongue depressor.

Another class of devices which employ tongue depressors for depressing a tongue are commonly called atomizers. Atomizers generally comprise a tube connected to an air bulb and a bottle containing a fluid, generally comprising medication. In use, the bulb is squeezed with sufficient force and speed so as to discharge a relatively high-velocity jet of air across an opening leading from the bottle. The relatively high-speed air creates a vacuum in the opening causing the fluid in the bottle to be sucked from the bottle and discharged with the air out the end of the tubular member. This is done while the tubular member is inserted in a person's mouth. The atomizers which employ a tongue depressor use the depressor for depressing the tongue so as to remove the tongue for more convenient and effective manipulation of the atomizer and direction of the spray. An atomizer of the type referred to is described in the patent to Hill et al., U.S. Pat. No. 862,737, dated Aug. 6, 1907 and the patent issued to Blackman, U.S. Pat. No. 487,873, dated Dec. 13, 1892. Because most atomizers, at least those used by the general public, are not inserted into the mouth to such an extent that they elicit significant gag reflexes, anesthesia is not generally required.

Another device which involves retracting a tongue during the use of the device is an emergency airway-providing device, which is generally used in unconscious persons for mouth-to-airway resuscitation. A device of this type is disclosed in U.S. Pat. No. 3,013,554, issued Dec. 12, 1961.

Referring in particular to the devices used for administering medication to the throat and pharyngeal areas, it may be noted that the means employed for administering medication and insuring that the medication reaches the rearmost and lowest portions of the throat is a relatively long, tubular member. As the tubular member is shortened, control over the distribution of the medication in the throat is reduced. With present-day inhalers using relatively short and relatively large mouthpieces, there is practically no control over the direction of the medication imparted to the throat, such that the medication can coat areas not intended to be coated. Depending on the type of nebulized medication employed, this may result in tingling sensations on a patient's tongue and even the development of a yeast infection.

While some of the above described devices employ a tongue retractor on incidentally retract a tongue when in use, none of the devices permits a person's lips to form about the device in an air-tight manner so as to prevent the passage of air between the lips and the device. All of the devices which use a tongue retractor placed far into a person's throat require that the person either be unconscious or that the throat and tongue area be anesthetized so as to prevent the elicitation of a significant gag reflex. None of the devices has a tongue retractor which is adjustable to accommodate different sized mouths. And, none of the devices is usable for evaluating a person's respiratory processes.

A mouthpiece used for evaluating a person's respiratory processes is disclosed in applicant's U.S. Pat. No. 3,742,939, issued July 3, 1973.

Referring to applicant's aforementioned patent, there is described in the specification, and shown in FIG. 7 thereof, a mouthpiece comprising a tubular member having a narrowed portion and a side port. The narrowed portion is provided to be inserted in a person's mouth.

In use, the mouthpiece is connected to a conventional spirometer and kymograph for measuring nasal or tracheobronchial airway resistance. When inserted in the mouth, the lips are closed about the narrowed portion of the tubular member of the mouthpiece in an air-tight manner.

During respirometry using the mouthpiece, inconsistent and unexplained deviations from expected results were observed. In a study of the observed results, it was found that the forced expiratory volume measured in a conventional manner was 2957 milliliters per second. When this determination was repeated with the tongue in front of the readily accessible mouthpiece, the one-second forced expiratory volume was 2558 milliliters per second. The difference was 399 milliliters per second, though the breaths were comparable.

In addition to permitting a person's tongue to obstruct the air flow therefrom, the prior known mouthpiece is also believed to adversely affect the air flow therefrom when it is used with a person having a trachea which is larger than the cross-sectional area of the mouthpiece. This is because the smaller mouthpiece will provide resistance to the air flow which can be interpreted as patient airway resistance.

SUMMARY OF THE INVENTION

In view of the foregoing, a principal object of the present invention is to provide a mouthpiece comprising a tubular member, about which a person may place his lips in an air-tight manner, and a tongue retractor for diagnosing and treating conditions of the throat and for evaluting a person's respiratory processes.

Another object of the present invention is a mouthpiece as described above having an annular lip for aiding the formation of an air-tight seal between the lips and the tubular member.

Another object of the present invention is a mouthpiece as described above for use in evaluating a person's respiratory processes in which the tubular member has a principal air passageway which has a cross-sectional area which, relative to the cross-sectional area of the trachea of the person using the mouthpiece, is large enough so as not to significantly affect the then current physiology of the respiratory process being evaluated in that person.

Another object of the present invention is a mouthpiece as described above having a tongue retractor the shape of which is adjustable to fit the mouth of a person so as not to elicit a significant gag reflex of the person's tongue or soft palate and to fit comfortably between the interior edges of the person's teeth and gums along the right and left sides of the lower jaw.

Another object of the present invention is a mouthpiece as described above, for administering medication to a user thereof having interior walls including means for directing an air flow therefrom to the rearmost and lowermost portions of the user's throat.

Another object of the present invention is a mouthpiece as described above having a side port.

DESCRIPTION OF THE DRAWINGS

The above and other objects, features and advantages of the present invention will become apparent to those skilled in the art from the following detailed description of the accompanying drawings in which:

FIG. 5 is an end view of the apparatus of FIG. 2.

FIG. 6 is an embodiment of the present invention comprising internal straight vanes.

FIG. 7 is an embodiment of the present invention comprising twisted vanes.

FIG. 8 is an embodiment of the present invention comprising internal gun-barrel rifling.

FIG. 9 is a plan view of a plug for plugging a mouthpiece according to the present invention.

FIG. 10 is an elevation view of FIG. 9.

DETAILED DESCRIPTION

Figure 1:
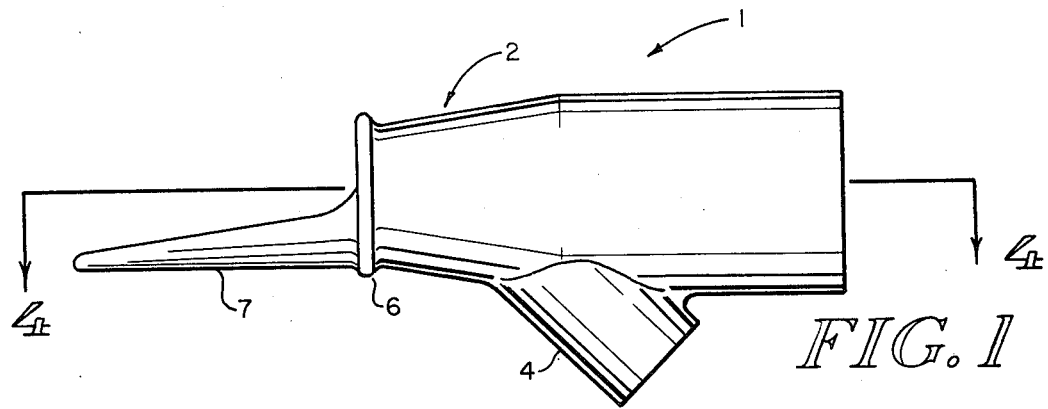
FIG. 1 is an elevation view of a mouthpiece according to the present invention.
Figure 2:
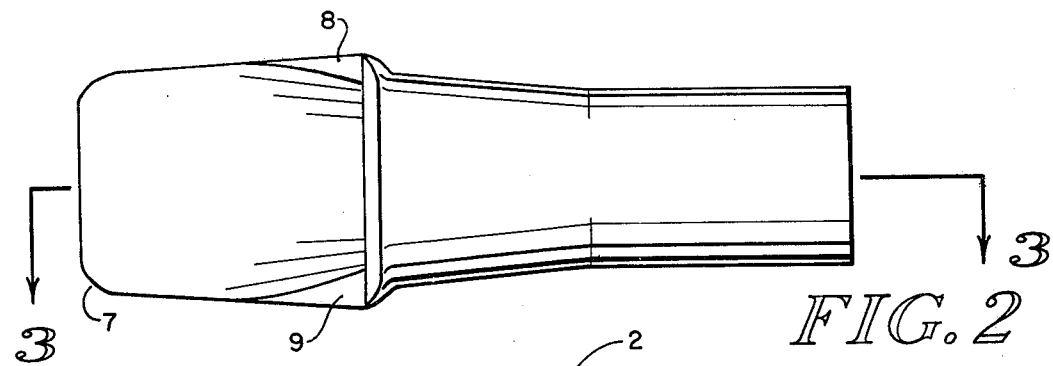
FIG. 2 is a top plan view of the apparatus of FIG. 1.
Figure 3:
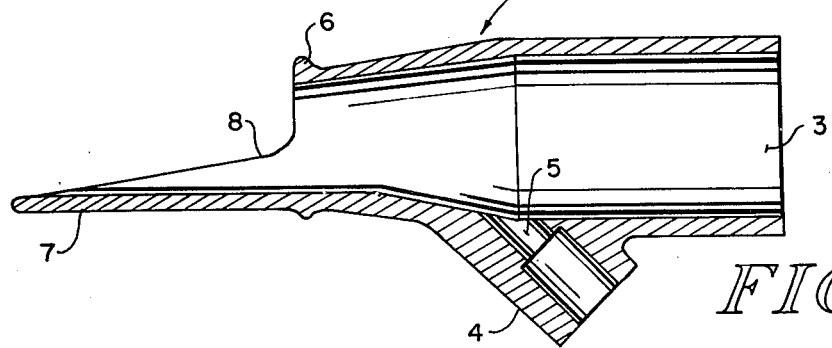
FIG. 3 is a cross-sectional view taken along lines 3—3 of FIG. 2.
Figure 4:
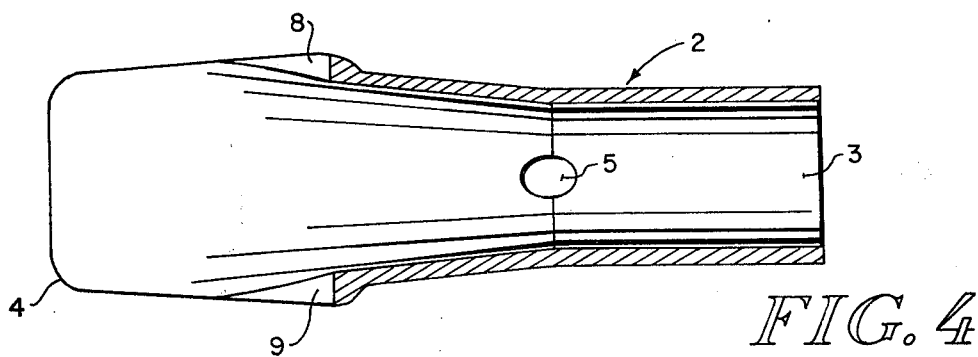
FIG. 4 is a cross-sectional view taken in the direction of lines 4—4 of FIG. 1.

Referring to FIGS. 1-5, there is provided, in accordance with the present invention, a mouthpiece designated generally as 1 comprising a tubular member 2 forming a principal air passageway 3. Extending from the principal air passageway 3 in the tubular member 2 there is a side port 4, forming a secondary air passageway 5. Port 4 extends from the tubular member 2 at an angle approximately 45° and is provided for connecting external equipment to the mouthpiece as by tubular members not shown, in any conventional manner. At the left end of the tubular member 2 there is provided an annular lip 6. Lip 6 extends about the tubular member 2. Extending from the lip 6, to the left of the lip 6, as seen in FIG. 1, there is provided a blade-like member forming a tongue retractor 7. The tongue retractor 7 is curved along the lateral edges 8 and 9 thereof and preferably comprises a material which can be adjusted or otherwise formed as by bending or carving to fit comfortably between the interior edges of a person's teeth and gums of the left and right sides of the lower jaw so as to fit the mouth of the person and not elicit a significant gag reflex from the person's tongue or soft palate.

In practice, while the shape of the tubular member 2 may be circular or rectangular in transverse cross section so as to conform more closely to the shape of a person's mouth, the cross-sectional area of the principal air passageway in the tubular member relative to the cross-sectional area of the airway formed by the trachea of the intended user of the mouthpiece should be large enough so as not to significantly affect the then current physiology of the respiratory process being evaluated in that person. The reason for this requirement is that, if the cross-sectional area of the tubular member is not large enough, the resistance to air flow and the effect on the respiration of the person using it will not permit a true measure of airway resistance and will adversely affect the evaluation of other respiratory processes.

While the tongue retractor portion 7 is preferably constructed of material which can be easily formed either by bending, shaping or carving, the tubular member 2 and side port 4 may comprise any suitable material compatible with any medication or the like used therewith, as well as with any other apparatus to which the mouthpiece is connected. In this regard, it is contemplated that the tubular member 2 may be made of a reusable material and that the tongue retractor portion 7 may be made of a disposable material which is removably attached to the tubular member 2 prior to use.

It is important in the administration of medication to insure that the medication reaches the area intended to be medicated and does not coat areas not intended to be medicated. This is important to avoid waste and to avoid undesired side effects, such as tingling sensations, numbing, the development of yeast infections and the like in a person's mouth and throat area. For this purpose, gun-barrel rifling, straight and twisted vanes in the interior walls of the tubular member 2 are employed.

Referring to FIG. 6, there is provided a mouthpiece 30 having a tubular member 32. In the interior walls of the tubular member 32 there is provided a plurality of vanes 33. The vanes 33 extend about ⅛ inch in height and extend radially toward the axis of the tubular member 32 for reducing any tendency of the air stream to assume a twisting flow.

Referring to FIG. 7, there is provided still another embodiment of the present invention comprising a mouthpiece 40. The mouthpiece 40 comprises a tubular member 42. Extending from the interior walls of tubular member 42, there is provided a plurality of vane members 43. The members 43 are about ⅛ inch in height and are substantially identical to the members 33 of FIG. 6 except that the members 43 are curved so as to describe a helical path on the interior wall of the member 42. The helical path of the vanes 43 is provided for inducing a vortex in the air stream exiting from the tubular member 42 which is sufficient to cause a narrowing of the air stream in a person's throat for localizing the administration of medication therein.

Referring to FIG. 8, there is provided in another embodiment of the present invention a mouthpiece 51 comprising a tubular member 52 and a plurality of relatively shallow grooves 53. The grooves 53, which are typically ⅛ inch deep, are formed in the walls of the member 2 in a helical fashion commonly known as gun-barrel rifling. The rifling is provided for imparting to air stream flowing therethrough a twisting motion for inducing a vortex in the air stream exiting the tubular member, which is sufficient to cause a narrowing of the air stream in a person's throat. The number of grooves 53 and the amount of twisting employed may be varied according to the effect desired.

Referring to FIGS. 9 and 10, there is provided a plug member 60. Plug member 60 comprises a flanged portion 61, a D-shaped handle member 62 and a plugging portion 63. The plug member 60 may comprise any suitable resilient material such as rubber, plastic or the like. The size and shape of the plugging portion 63 corresponds to the size and shape of the interior of the end of the tubular member 2 opposite the tongue retractor portion 7 for plugging the tubular member 2. A similar plug member, but with a smaller diameter, may be employed for plugging the side port of the mouthpiece. When used for plugging the mouthpiece of FIGS. 6, 7 and 8, the diameter of the plugging portion 63 is typically slightly larger than the smallest distance between opposing vanes and the diameter of the flange portion 61 is large enough to cover all vanes and the intermediate air passageways.

In use, any of the mouthpieces according to the present invention may be coupled to a spirometer and kymograph in any suitable manner and used in the manner and for the purpose described in applicant's above described U.S. Pat. No. 3,742,939. Because of the presence of the tongue retractor, however, it may be expected that the accuracy of the measurements made will be improved from that obtained using the prior known mouthpiece.

Referring to FIGS. 1-5, depending on the type of measurements and evaluations conducted, either the main tubular member 2 or the side port 4 may be removably plugged by plugs as described with respect to FIGS. 9 and 10.

For use in the administration of medication, the mouthpieces, likewise, may be coupled in any conventional manner to suitable apparatus and either the main port of the tubular member 2 of the side port 4 may be plugged, depending on the particular treatment being given.

In general, after a mouthpiece is coupled to the desired apparatus, plugged or unplugged as required, and the tongue retractor 7 has been shaped as by bending, or carving to fit the person's mouth so as not to elicit a significant gag reflex, it is inserted in the person's mouth until the teeth of the person rest on the interior surface of the lip 6. The lips of the person are then voluntarily closed about the tubular member 2 for forming an airtight seal therewith. When the mouthpiece is comfortable and inserted as described, the evaluation or treatment can then proceed.

Several embodiments of a mouthpiece according to the present invention are described. It is contemplated, however, that other changes and modifications in the composition and structure of the embodiments described will occur to those skilled in the art and may be made without departing from the spirit and scope of the present invention. It is, therefore, intended that the present invention be not limited to the embodiments described but rather be determined by reference to the claims hereinafter provided and their equivalents.

What is claimed is:

1. A mouthpiece with a tongue retractor, comprising:
    an open ended tubular member defining an air passage including means at one end insertable in a conscious person's mouth and about which said person may voluntarily place his lips in an air-tight manner for preventing a passage of air between said lips and said tubular member an opposite end of said tubular member adaptable for use in evaluating a persons respiratory process; and
    means forming a tongue retractor having a blade-like shape extending from an edge of said one end of said tubular member substantially parallel to the wall of the tubular member and non-obstructive to air exiting the air passage, said tongue retractor restricting the movement of said person's tongue and preventing it from obstructing a flow of air through said tubular member.

2. A mouthpiece according to claim 1 wherein said tubular member has a cross-sectional area which, relative to the cross-sectional area of the trachea of the person using the mouthpiece, is large enough so as not to significantly affect the then current physiology of the respiratory process being evaluated in the person.

3. A mouthpiece according to claim 1 intended for use by an identifiable group of persons wherein said tubular member has a cross-sectional area which is substantially equal to or larger than the average cross-sectional area of the trachea of all of the persons in the group so as not to significantly affect the then current physiology of a respiratory process being evaluated in a person from the group.

4. A mouthpiece according to claim 1 for use in evaluating a person's respiratory processes in which said tubular member has a transverse cross-sectional area which is large enough to have an insignificant effect on the then current physiology of the respiratory process being evaluated in the person.

5. A mouthpiece according to claim 1 wherein said tubular member includes an annular lip about the end of the tubular member at the tongue retractor edge, said lip forming a surface against which a person's teeth may be placed for retaining the mouthpiece in his mouth.

6. A mouthpiece according to claim 1 wherein said tongue retractor comprises means for changing the shape of the retractor to fit the mouth of said person so as not to elicit significant gag reflex from said person's tongue or soft palate and to fit comfortably between the interior edges of the person's teeth and the gums of the lower jaw.

7. A mouthpiece according to claim 6 wherein said means for changing the shape of said tongue retractor comprises a material which can be carved to a desired shape.

8. A mouthpiece according to claim 6 wherein said means for changing the shape of said tongue retractor comprises a material which can be bent to a desired shape.

9. A mouthpiece according to claim 1 wherein said tubular member comprises means in the interior walls thereof for changing the dimensions of an airstream as it passes through the tubular member.

10. A mouthpiece with a tongue retractor comprising:
 a tubular member, including means insertable in a conscious person's mouth and about which said person may voluntarily place his lips in an air-tight manner for preventing a passage of air between said lips and said tubular member;
 means having a blade-like shape extending from an edge of said tubular member and forming a tongue retractor for restricting the movement of said person's tongue and preventing it from obstructing a flow of air through said tubular member; and
 means forming a side port in said tubular member for adding something to or measuring the pressure of an airstream passing through said tubular member.

11. A mouthpiece according to claim 10 comprising:
 means for closing the exterior end of said tubular member; and
 means for closing said side port for making predetermined measurements depending on which of said closing means is employed.

12. A mouthpiece with a tongue retractor comprising:
 a tubular member including means insertable in a conscious person's mouth and about which said person may voluntarily place his lips in an air-tight manner for preventing a passage of air between said lips and said tubular member;
 means having a blade-like shape extending from an edge of said tubular member and forming a tongue retractor for restricting the movement of said person's tongue and preventing it from obstructing a flow of air through said tubular member; and
 means for inducing a vortex in the airsteam exiting the tubular member sufficient to cause a narrowing of the air-stream in the person's throat.

13. A mouthpiece according to claim 12 wherein said inducing means comprises gun barrel-type rifling.

14. A mouthpiece according to claim 12 wherein said inducing means comprises a plurality of twisted vane-like members which describe a helical-type rotation within the interior of said tubular member.

* * * * *